United States Patent
Ortiz Niembro et al.

(10) Patent No.: US 8,956,630 B2
(45) Date of Patent: Feb. 17, 2015

(54) ABSORBENT COMPOSITION FOR SURFACE TREATMENT

(71) Applicants: Jose Antonio Ortiz Niembro, Puebla (MX); Francisco Boker, Mexico City (MX)

(72) Inventors: Jose Antonio Ortiz Niembro, Puebla (MX); Francisco Boker, Mexico City (MX)

(73) Assignee: Sued-Chemie IP GmbH & Co. KG, Munich (DE)

( * ) Notice: Subject to any disclaimer, the term of this patent is extended or adjusted under 35 U.S.C. 154(b) by 0 days.

(21) Appl. No.: 13/682,864

(22) Filed: Nov. 21, 2012

(65) Prior Publication Data
US 2013/0143740 A1    Jun. 6, 2013

Related U.S. Application Data

(62) Division of application No. 12/514,603, filed as application No. PCT/EP2007/009596 on Nov. 6, 2007, now abandoned.

(30) Foreign Application Priority Data

Nov. 13, 2006   (EP) ..................................... 06023561

(51) Int. Cl.
| | | |
|---|---|---|
| A61K 9/00 | (2006.01) |
| A01N 25/00 | (2006.01) |
| A61K 9/14 | (2006.01) |
| A01K 13/00 | (2006.01) |
| A61C 3/03 | (2006.01) |
| B01J 20/12 | (2006.01) |
| B01J 20/28 | (2006.01) |

(52) U.S. Cl.
CPC ................. *A61K 9/14* (2013.01); *A01K 13/001* (2013.01); *A61C 3/03* (2013.01); *A61K 9/0017* (2013.01); *B01J 20/12* (2013.01); *B01J 20/28004* (2013.01); *B01J 20/28019* (2013.01); *B01J 20/2803* (2013.01); *B01J 20/28057* (2013.01); *B01J 20/28071* (2013.01)
USPC .......................... 424/400; 424/405; 504/116.1

(58) Field of Classification Search
USPC ................................ 424/400, 405; 504/116.1
See application file for complete search history.

(56) References Cited

U.S. PATENT DOCUMENTS 4,500,670 A  *  2/1985  McKinley et al. ............ 524/445
5,402,752 A      4/1995  Hähn et al.

(Continued)

FOREIGN PATENT DOCUMENTS

CN           1505472 A       6/2004
DE    10 2004 060 587 A1     7/2004

(Continued)

OTHER PUBLICATIONS

Elliott P. Barrett et al., "The Determination of Pore Volume and Area Distributions in Porous Substances. I. Computations from Nitrogen Isotherms," *Journal of American Chemical Society*, vol. 73, 1951, pp. 373-380.

(Continued)

*Primary Examiner* — Blessing M Fubara
(74) *Attorney, Agent, or Firm* — RatnerPrestia

(57) ABSTRACT

The invention concerns an absorbent composition comprising: (a) at least 50 wt.-% of the overall composition have a particle size of less than 150 .mu.m and are comprised of at least one absorbent component; and (b) at least 1.0 wt.-% of the overall composition have a particle size of at least 250 .mu.m and are comprised of at least one particulate component, and its preferred uses.

23 Claims, 1 Drawing Sheet

(56) References Cited

U.S. PATENT DOCUMENTS

| | | | |
|---|---|---|---|
| 5,450,817 | A | 9/1995 | Hähn et al. |
| 5,860,391 | A | 1/1999 | Maxwell et al. |
| 2003/0086974 | A1* | 5/2003 | Besemer et al. ............... 424/484 |
| 2005/0250896 | A1* | 11/2005 | Ratzsch et al. ................ 524/500 |
| 2005/0279474 | A1* | 12/2005 | Sanne et al. .................. 162/158 |
| 2006/0201391 | A1 | 9/2006 | Scialdone |
| 2008/0213455 | A1 | 9/2008 | Demais et al. |
| 2009/0044921 | A1 | 2/2009 | Sohling et al. |

FOREIGN PATENT DOCUMENTS

| | | |
|---|---|---|
| WO | WO 2006/030075 A1 | 3/2006 |
| WO | WO 2006/079221 A1 | 8/2006 |

OTHER PUBLICATIONS

Anonymous (Corporate Profiles): OLMIX—The Maker of Mistral; Pig International 2005; pp. 43-43; vol. 35, No. 5; Watt Publishing Co., Mount Morris, Illinois, USA.

Darrell Rothlisberger, "Basic Show Pig Feeding and Care," Internet Article, 2005; pp. 1-6, Utah State University Extension Publications, URL: https://EXTENSION.USU.EDU/FILES/PUBLICATIONS/BASIC%20Show%2OPIG.PDF.

Arno Schramme, "Über Handwaschpasten und andere Handreinigungsmittel," Seifen-Öle-Fette-Wachse, vol. 91, No. 12; 1965; pp. 389-393.

Nicole M. Stark et al., "Effect of Species and Particle Size on Properties of Wood-Flour-Filled Polypropylene Composites," Functional Fillers for Thermoplastics & Thermosets, 1997; pp. 2-21, Presentation at Conference, Dec. 8-10, 1997, San Diego, CA USA.

Adam Traczykowski et al., "Effect of the Mistral Preparation on Somatic Cells in Milk Cows," *Proceedings of the XIIth International Congress on Animal Hygiene*, 2005; pp. 324-326; vol. 1, Warszaw, Poland.

European Search Report of EP 06 02 3561, dated May 10, 2007.

International Search Report of PCT/EP2007/009596, dated Jan. 3, 2008.

* cited by examiner

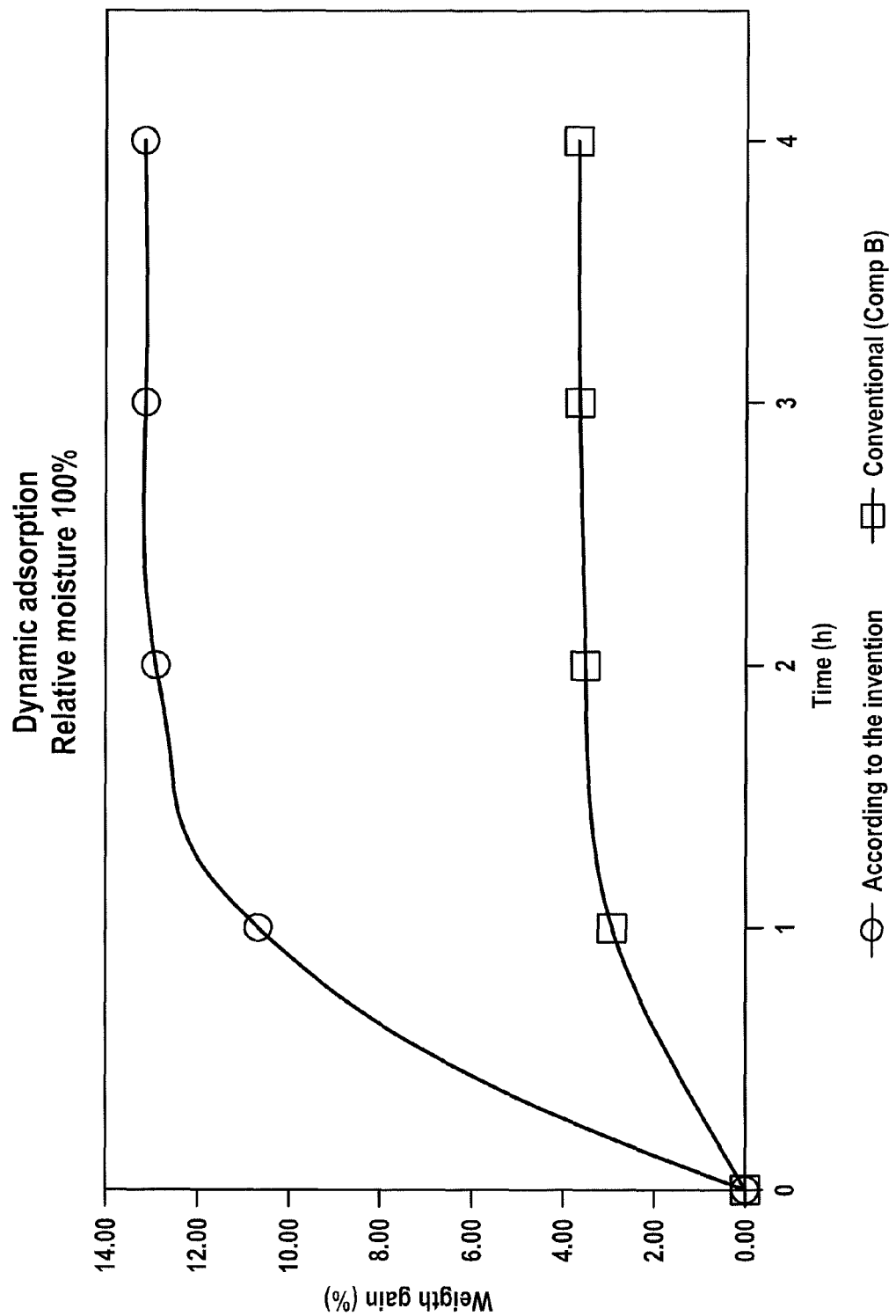

ABSORBENT COMPOSITION FOR SURFACE TREATMENT

CROSS REFERENCE TO RELATED APPLICATIONS

This application is a divisional application of U.S. patent application Ser. No. 12/514,603, filed Jan. 26, 2010, which is a U.S. National Phase Application under 35 U.S.C. §371 of International Patent Application No. PCT/EP07/009596, filed Nov. 6, 2007, which claims priority benefit from European Application No. 06023561.1, filed Nov. 13, 2006, the contents of all of which are incorporated by reference herein.

BACKGROUND OF THE INVENTION

The invention discloses an absorbent composition and its preferred use, in particular for the treatment of a surface.

A number of different absorbent compositions are known in industrial, household and agricultural applications. In general absorbents are used for the removal of different toxic and non-toxic gaseous and liquid substances.

There exists a great demand for new absorbent compositions adapted for optimum performance, safe, economic, biologically acceptable and easy use, especially on the field of animal and/or livestock breeding, farming and husbandry. Keeping healthy animals, especially if at great numbers in a limited space requires clean and dry conditions. Therefore it is necessary to keep the stable, its surfaces as well as the animals itself clean and dry. Especially new-born animals are very sensitive to temperature loss resulting from wet conditions and infections due to microbiological and other contamination which occur much more easily if their skin and/or their environment (surfaces) are moist or wet. For example, the time between birth and first colostrums intake of piglets depends directly on the overall constitution of the new born animal. This first milk is especially rich on antibodies and therefore has a great influence on the piglet's immune system. Especially the remaining birth liquids on the animal's skin negatively affect the animal health due to a significant temperature loss during the slow drying process and an increased infection risk. These conditions lead to longer periods of time between birth and first colostrums intake and increased health risks. Furthermore, the sow is able to produce the colostrum only for a short period of time. Therefore it is necessary to dry and clean the newborn animals as fast as possible.

The prior absorbent compositions are frequently not suitable for a direct surface treatment including cleaning and drying and are not optimized for such application, especially for application and effectiveness on an animal skin. Many known compositions are difficult to apply or do not form a uniform and protective cover on the surface. Also, many known absorbent compositions are difficult to distribute on the surface to be treated and/or to be removed form the hands of the user after application. Furthermore, known absorbent compositions are not adapted for optimum performance, safe, economic, biologically acceptable and easy use in the treatment of surfaces, especially in the field of animal and/or livestock breeding, farming and husbandry.

SUMMARY

Therefore, it is a first objective of the present invention to provide an absorbent composition which avoids the disadvantages of the prior art, and which is especially suitable for the treatment of surfaces, in particular the skin of animals.

According a first aspect, the invention provides an absorbent composition which comprises at least two components, namely a (preferably powdery) absorbent component with a small particle size which constitutes the major fraction of the overall composition, and a second particulate component with a greater particle size compared to the first component, and which constitutes a smaller fraction of the overall composition as compared to the first component. Thus, according to one aspect of the invention it was surprisingly found that an absorbent composition comprising those two components is particularly suitable for the treatment of surfaces, in particular the skin of an animal.

It has also been surprisingly found that the compositions of the invention show improved applicability to and effectiveness on an animal skin. They can easily be applied or distributed as a uniform and protective cover on the surface. The component with the greater particle size (as described in detail herein) allows an easy distribution and at the same time has a "massaging" effect, which contributes to quick and complete drying of the surface, e.g. the skin of a new-born animal, and to increased blood circulation in the skin. This considerably helps to keep the animal warm and healthy, together with the smaller particle size component as further described herein. In other words, the small particle size component and the greater particle size component act together synergistically when applied to a surface. Furthermore, if desired, the composition of the invention is easy to be washed off from the hands of the person applying it, as the greater particle size component may act as a "frictioning agent". Thus, the present absorbent compositions are adapted for optimum performance, safe, economic, biologically acceptable and easy use in the treatment of surfaces, especially in the field of animal and/or livestock breeding, farming and husbandry.

DETAILED DESCRIPTION

According to one aspect, the invention is directed to an absorbent composition wherein: (a) at least 50 wt.-% of the overall composition have a particle size of less than 150 µm and are comprised of at least one absorbent component; and (b) at least 1.0 wt.-% of the overall composition have a particle size of at least 250 µm, preferably at least 400 µm, and are comprised of at least one particulate component.

The term "absorbent" shall include all mechanisms of absorption and adsorption, as well as chemisorptions, and shall be used interchangeably with these terms.

Such a composition is claimed in claim 1. Preferred embodiments are defined in the depending claims.

The absorbent component (a) can principally comprise any known inorganic and/or organic absorbent material including mixtures thereof. Non-limiting examples of inorganic absorbent materials include clays, silica gel, diatomic earth and zeolithe. These materials can be partially or wholly modified with e.g. acids, or cations like sodium or calcium or organophilic substances like quaternary ammonium salts. It has been found that inorganic absorbents, especially clay-type absorbents are particularly suitable for the present invention. In addition to a high absorption capacity they can provide an advantageous cover or coating on an animal skin which keeps the animal both dry and warm. Clay-type absorbents may include natural and synthetic (layered) silicates, e.g. two and three layered silicates like serpentine, kaoline, smectite, vermiculite and chlorite. Preferably, the clay-type absorbent is selected from the group of phyllosilicates, in particular smectite clays such as bentonite. This includes natural occurring clays and modified clays. Examples of modified clays are clays treated with acid or soda. Also by replacing multivalent ions like $Ca^{2+}$ in the interlayer space, the absorption properties of the clay can be modified. Preferably, the absorbent component is used in dry or dried form having a moisture content (determined as set out below) of less than 25 wt-%, preferably less than 20 wt-%, in particular less than 10 wt-%.

Non-limiting examples of suitable organic absorbent materials include e.g. cellulose containing materials like paper, waste paper, straw, wood chips and saw mill dust. However, inorganic materials are preferred and have been found to minimize health risks to new-born animals better than compositions with organic absorbents. According to one particular embodiment, the absorbent composition therefore does not contain organic absorbents.

According to one preferred aspect of the invention, the absorbent composition and/or the absorbent component has a BET surface area of at least 50 $m^2/g$, preferably at least 100 $m^2/g$, more preferably at least 150 $m^2/g$, more preferably at least 180 or at least 200 $m^2/g$. The high surface area of the absorbent component/the absorbent composition has been found to be of particular advantage for the treatment of the skin of an (new-born) animal.

Preferably, the absorbent composition and/or the absorbent component contained therein has a water absorption of at least 25%, preferably at least 35%, more preferably at least 45%, more preferably at least 50%.

According to a particularly preferred aspect of the invention, the absorbent composition and/or the absorbent component contained therein has an oil absorption of at least 20%, preferably at least 25%, more preferably at least 30%, more preferably at least 35%. Thus, it has been surprisingly found that components or compositions with a high oil absorption are particularly useful in the treatment of animal skin and allow most rapid drying e.g. of amniotic fluids on the skin of a new-born animals (for example a piglet). It appears that the absorption of lipophilic components on the surface/skin allows also more rapid and complete absorption of the hydrophilic components and water on the skin. According to one embodiment of the invention, the absorbent component and/or the composition of the invention itself has an oil absorption as defined above. According to another embodiment of the invention, the absorbent component and/or the composition of the invention itself has an oil absorption according to DIN 53199 of more than about 90 g/100 g, preferably more than about 100 g/100 g, preferably more than about 110 g/100 g, in particular more than about 120 g/100 g. Also, it was found that the oil absorption and water absorption properties of the composition (the components contained therein) act together in a synergistic manner.

One preferred aspect of the invention is directed to the use of a component having an oil absorption as described herein in an absorbent composition, irrespective of the particle size of the component and other components present in the absorbent composition. This aspect of the invention thus refers also to a composition of the invention as described herein, but not necessarily showing the particular particle size of the absorbent component, and the presence and particle size of the particulate component.

Preferably, the absorbent composition and/or the absorbent component contained therein has a dynamic water adsorption of at least 5%, preferably at least 8%, more preferably at least 10%, more preferably at least 12%.

It is also preferred, that the absorbent composition and/or the absorbent component contained therein has a total pore volume of at least 0.1 ml/g, preferably at least 0.2 ml/g, more preferably at least 0.3 ml/g, more preferably at least 0.4 ml/g, more preferably at least 0.5 ml/g.

Also, it has been found that particularly effective compositions are provided, if the absorbent composition and/or the absorbent component contained therein have a cation exchange capacity (CEC) of at least 30 meq/100 g, preferably at least 50 meq/100 g. The CEC is assumed to help in the rapid and simultaneous adsorption or absorption of a great variety of substances on the treated surface, e.g. of amniotic fluid on the skin of a new-born animal.

The absorbent composition further includes at least one particulate component with a particle size of at least 250 µm, preferably at least 400 µm in an amount of at least 1.0 wt.-% of the overall composition. In other words, at least 1.0 wt.-% of the overall composition consist of particles having a particle size of at least 250 µm, preferably 400 µm. Like the absorbent component, the particulate component can be selected from a variety of solid organic and inorganic materials. According to a preferred embodiment, similar or the same materials as described above for the absorbent component will be used for the particulate component. The particle size has been found to be advantageous in the use of the composition for the treatment of surface (see supra). However, according to one embodiment, especially if the absorption properties and the amount of absorbent component in the composition are high enough for the particular requirements, non-absorptive or weakly absorptive materials like e.g. carbonates or sulfates such as $CaCO3$, $CaSO_4$ or $MgCO_3$ can also be used as the particular component. Mixtures of more than one material may also be used. Preferably the particulate component is also a water absorbing component.

It has been found that preferably the particulate component should be present in the composition of the invention in an amount of at least 2 wt.-%, more preferably at least 5 wt.-%, more preferably at least 8 wt.-% of the overall composition. In a broad sense, the particulate component constitutes less than 50 wt.-%, of the overall composition. However, in many cases it has been found to be of advantage if the amount of particulate component in the composition is not too high. Thus, preferably, the particulate component is present in an amount of not more than about 20 wt.-%, preferably not more than about 15 wt.-% of the overall composition.

According to a preferred embodiment of the invention, the particulate component has a particle size of at least about 600 µm, preferably at least about 800 .mu.m, more preferably at least about 1000 µm. It is also preferred that the particulate component has a particle size of less than 5 mm, more preferably less than 2.5 mm.

It has been found that the effects of the particulate component are most beneficial, if it has an aspect ratio between about 1 and about 3, preferably between about 1 and about 2, more preferably about 1 and about 1.5. The aspect ratio is defined as the ratio of its longest dimension to its shortest dimension. Such a form also prevents smearing or damaging of the surface to be treated. Preferably, the particulate component has a round or rounded shape, preferably a spherical or substantially spherical shape.

According to a preferred aspect of the invention, the absorbent component is in powder form and preferably has a particle size (D90, preferably D99) of not more than 400 µm, preferably not more than 300 µm, more preferably not more than 250 µm. The notation D90 (D99) of not more than x µm means, that 90 (99) volume percent of the particles have a size smaller than x µm. A detailed description of measuring the particle size is given below.

The absorbent component constitutes at least 50 wt.-%, preferably at least 60 wt.-%, more preferably at least 75 wt.-%, more preferably at least 85 wt.-% of the overall composition.

According to a preferred embodiment the particulate component comprises a clay material, preferably a phyllosilicate clay material, in particular bentonite, preferably in agglomerate or granulate form.

According to a further preferred embodiment of the invention, the particulate component has a swellability of less than 10 ml/2 g, in particular less than about 8 ml/2 g. In many cases this can improve the effect to keep the particulate component in its desired shape for a sufficient time upon contact with water and other substances to be absorbed.

According to a further preferred embodiment of the invention, the particulate component has an attrition value of no more than 5%. In many cases this may improve the effect to keep the particulate component in its desired shape and functionality for a sufficient time during application onto the surface.

The composition of the invention may substantially or completely consist of the components mentioned above. However, depending on the particular intended use, further components may be present, especially components providing additional properties to the composition. Thus, according to one embodiment, the absorbent composition may further comprise at least one component selected from the group of fragrances or perfumes, biocides, fungicides, herbicides, sanitizers or fillers. These components can be selected according to the specific application and can be combined and varied independently.

According to one embodiment of the present invention, the composition has a pH value, measured in a suspension of 10 parts by weight of the composition in 100 parts by weight water, of at least about 7, preferably at least about 8, preferably at least about 8.2. A basic pH value can be helpful to neutralize acidic liquids like urine and organic acids, therefore lowering the harmful properties of these liquids or their metabolites. However, it is clear to the skilled person that the pH value of the composition will be adjusted in a range which avoids harm or damage to the surface to be treated. Thus, too acidic and too basic pH values should be avoided if the composition is to be applied onto the skin of an animal.

As stated above, the absorbent composition of the invention is preferably used for the treatment of a surface. Generally, this includes biological and non-biological surfaces like floors, ceilings and walls, e.g. in animal environments like stables or boxes. A particularly preferred use of the composition of the invention is for the adsorption of amniotic and other body fluids or liquids of animals. Amniotic fluid is the liquid surrounding and cushioning a growing fetus within the amnion. It contains proteins, carbohydrates, lipids and phospholipids, urea and electrolytes. The absorbent composition is particularly suitable to absorb such fluids or liquids. A fast removal of amniotic liquid after the birth of an animal by using the composition of the invention significantly reduces the dangerous cooling down of the new born animal caused by the drying process of the amniotic liquid and also the consequent risks of later infections. It can also reduce the time between births and first colostrums intake, can lead to a faster drop of the umbilical (naval) cords, and may inhibit the proliferation of molds, viruses and bacteria. Thus, it may e.g. help to greatly reduce the animal's losses in a farrowing unit.

As set out above, the absorbent composition according to the invention is preferably used for the treatment of the skin of an animal, in particular a farm or industrially farmed animal, in particular a new-born animal. Preferably, the absorbent composition is used for the treatment of a stable or farrowing unit. Preferably, the farm animals are selected from the group of pig, cattle, sheep, horses, goats or poultry.

According to a further aspect of the invention, the absorbent composition of the invention is used for the preparation of a treatment composition for the treatment of an animal, in particular the skin of an animal. Therefore the absorbent composition can be used as or in various treatment compositions for cleaning and drying animal skin as described above. Additionally it can be used for the preparation of compositions for the treatment of skin irritations or skin diseases caused by microorganisms and parasites like fleas, ticks, mite or louse. According to preferred aspects of the invention, the absorbent composition can be used for the treatment of a surface, for the treatment of the skin of an animal, in particular a farm or industrially farmed animal (e.g. a pig, cattle, sheep, horses, goats or poultry), in particular a new-born animal, for the absorption of amniotic fluid or for the treatment of a stable or farrowing unit, e.g. of the aforementioned animals.

A further aspect is directed to the use of an absorbent composition as described herein for the preparation of a treatment composition for the treatment of an animal, in particular the skin of an animal.

The composition of the invention may be prepared in any conventional way by mixing the components thereof in known mixing devices. It may be applied to the surface to be treated in any manner known to the skilled person, preferably in dry particulate form. The dosage will depend on the intended use. As an example only, about 500 g of the composition may be used for treatment of the skin of a litter of piglet, i.e. 8 to 14 piglets.

1.) Used Methods and Materials

The following methods may be used to determine the various parameters defined herein.

1.1) Specific Surface and Pore Volume

The specific surface and pore volume may be determined using a Autosorb-1MP vacuum volumetric gas sorption analyzer (Quantachrome Corp.) according to DIN 66131 (BET surface area) and according to E. P. Barret, L. G. Joiner, P. P. Haienda, J. Am. Chem. Soc. 73, 1951, 373 (pore volume according to BJH Method). The pore volume determined includes pores ranging from 1.7 to 300 nm. An automated Analyser obtained from Mikromeritics, Germany, Type ASAP 2010, may be used according to the instructions from the manufacturer.

1.2) Cation Exchange Capacity

The Cation Exchange Capacity (CEC) may be determined by treatment of the material to be tested (e.g. the clay material) with a large excess of aqueous $NH_4Cl$-solution, washing, and determination of the amount of $NH_4^+$ remaining on the material according to Kjeldahl. The method is explained in detail in DE 10 2004 060 587 A1 of the same applicant.

1.3) BET Surface Area

The specific surface area may be measured by the BET-method (single-point method using nitrogen, according to DIN 66131) with an automatic nitrogen-porosimeter of Micrometrics, type ASAP 2010.

1.4) Particle Size a) For the absorbent component: The particle size may be determined according to the Malvern method. A Mastersizer 2000 of Malvern Instruments Ltd, UK may be used according to the instructions from the manufacturer (Version 3.01). Measurements can be done in the applicable probe chamber ("dry powder feeder") in air and the determined values refer to volume percent of the samples. The D50 value indicates the particle sizes at which 50 vol-% of the probe have smaller particle sizes. The D90 value indicates the particle size at which 50 vol-% of the probe has a smaller particle size. From the vol.-%, the corresponding wt-% may be calculated.

b) For the particulate component: if the particles are too large for application of the above method a), the particle size may be determined according to dry mesh residue using meshes of different sizes (Mesh size US-Std.).

1.5) Water Absorption

The water absorption may be determined by suspending the material to be tested in water at 10% solids (the material to be tested is previously dried at 110° C. for 2 hours to eliminate the free moisture content). The suspension is agitated at 350 rpm for 20 min at room temperature. Then, the suspension is filtered through filter paper by gravity until no water is coming out of the filtering funnel. The filter cake is then weighed to calculate the water gain in % (based on the initial weight of the dried sample).

1.6) Oil Absorption

The oil absorption may be determined by the following method: The material to be tested is suspended in soybean oil at 10% solids (the material to be tested is previously dried at 110° C. for 2 hours to eliminate the free moisture content). The suspension is agitated at 350 rpm and 130° C. under atmospheric pressure for 20 minutes. Finally, the suspension is filtered under vacuum (380 mbar) for 10 minutes and the filter cake is weighted to calculate the oil weight gain in % (based on the initial weight of the dried sample).

1.7) Dynamic Moisture Absorption

The dynamic moisture adsorption of a sample (the sample material to be tested is previously dried at 110° C. for 2 hours to eliminate the free moisture content) may be determined by passing dry air through distilled water and then through the sample at atmospheric pressure and room temperature until constant weight to calculate the moisture gain in % (based on the initial weight of the dried sample).

1.8) Moisture Content

The moisture content of a sample may be determined in a moisture balance analyzer (Ohaus Mod MB200 obtained from OHAUS Corporation) at 180° C. until constant weight according to the manufacturer's instructions.

1.9) Carbonate Content

The carbonate content may be evaluated in a calcimeter (according to Dietrich and Fruhling procedure and apparatus). This method consists essentially of a sample-holder, one serpentine for cooling and one graduated cylinder with readings on the results of the neutralization reaction between the sample and the hydrochloric acid. Since the volume of $CO_2$ (carbonic anhydride) is in direct relation with the amount of $CaCO_3$ (carbonate contained in the sample) it is possible to calculate the amount of carbonates measuring the volume of $CO_2$ produced in the reaction.

1.10) Swellability/Swelling Volume (Sediment Volume)

A calibrated 100 ml-glass cylinder is filled with 100 ml dest. water. 2.0 g of the sample are added slowly in 0.1 to 0.2 g portions onto the water surface. The next portion is added after the previous one has sunk in the water. After all portions have been added and one hour has lapsed, the volume of the sample is measured in ml/2 g ab.

1.11) Attrition Value/Crushing Strength

The attrition value of the particulate component may be evaluated by putting 100 g sample of the granulated material into a 100 mesh (US STD) drip pan and cover together with 3 rubber 2.9 cm diameter balls. After 15 min treatment in the rotation sieve shaker the fine material passing through the mesh is weighted and calculated as % of fines which will be the attrition value.

1.12) pH Determination

A 10 wt.-% slurry of the clay material in destilled water is heated to the boiling point and then cooled to room temperature under a nitrogen atmosphere. The pH-value is determined with a calibrated glass-electrode.

The following examples will serve to illustrate certain embodiments of the herein disclosed invention. These examples should not, however, be construed as limiting the scope of the invention.

EXAMPLES

A composition according to the invention was prepared as follows.

As an absorbent component a clay material (Secasil, available from Sud-Chemie de Mexico, S. A., Puebla, MX) having a D50 particle size of 47 µm was used. The D90 value was 162 µm. The oil absorption according to DIN 53199 was above 120 g/100 g clay material. The further properties of the material used in accordance with the invention are evident from Table 1 below. Further alternative clays are such sold by Sud-Chemie under the trade name Terrana® 522 or as Ex MEX 1073 and 1561.

As the particulate component, aluminium silicate (bentonite) granules sold by Sud-Chemie de Mexico, S. A., Puebla, MX under the trade name "Red Speckles 414" having spherical shape were used. Their particle size ranges (to more than 95 wt-%) from about 1400 to 425 µm.

The aforementioned components were mixed in a conventional dry blender using 10 wt.-% of the particulate component and 90 wt.-% of the absorbent component to obtain a uniform mixture.

As a comparison (Comp. A), a composition only comprising the absorbent component (i.e. with no particulate component) was used.

As a further comparison (Comp. B), a conventional commercial product was used. The characteristics of this product are summarized in Table 1 below. It did not contain a particulate component as described above.

TABLE 1

|  | According to the invention | Conventional (Comp B) |
|---|---|---|
| Specific surface ($m^2/g$) | 213 | 34 |
| Pore volume ($cm^3/g$) | 0.593 | 0.092 |
| Water absorption (%) | 56.7 | 41.2 |
| Oil absorption (%) | 39.4 | 20.6 |
| Dynamic moisture absorption (%) | 13.1 | 3.6 |

The wet skin of a litter of new-born piglets (8 to 14 piglets) was manually treated with about 500 g of either of the above composition. It showed that it was much easier to uniformly apply the composition of the invention as compared to compositions Comp. A and Comp. B. Also, the skin of the piglets treated with the composition of the invention dried much faster and more uniformly upon application of the composition. The greatest difference was observed between the composition of the invention and Comp. B. The time until first colostrums uptake was significantly decreased when comparing the composition of the invention and Comp B. Comp A was less effective than the composition of the invention, but still superior to Comp. B. Similar results as with Comp. A were obtained when the composition of the invention was ground so that the particulate component contained therein has a particle size of less than 250 µm (Comp C). The handling properties of Comp. A, Comp. B and Comp. C were inferior as compared to the composition of the invention and not massaging effect on the skin of the animals was observed. Also, the drying of the piglet skin was slower (Comp B being the slowest by far).

BRIEF DESCRIPTION OF THE DRAWING

The advantages of the composition of the invention are further illustrated by FIG. 1, showing the dynamic water adsorption for the conventional composition (Comp. B) as compared to the composition according to the invention.

What is claimed:

1. A method for removing amniotic fluid from the skin of a newborn animal comprising applying an absorbent composition to the skin of the new-born animal wherein the absorbent composition comprises at least one phyllosilicate having a water-absorption of at least 25% and/or a dynamic water adsorption of at least 5% and at least one clay particulate having an aspect ratio between 1 and 3, wherein:
    a) at least 50 wt.-% of the overall composition comprises the at least one phyllosilicate and the at least one phyllosilicate has a particle size of less than 150 µm; and
    b) from 2 wt.-% to 20 wt.-% of the overall composition comprises the clay particulate component and the clay particulate composition has a particle size of at least 250 µm.

2. The method according to claim 1, wherein the at least one clay particulate component has a particle size of at least 400 µm.

3. The method according to claim 1, wherein the at least one clay particulate component is present in an amount of at least 5 wt.-% of the overall composition.

4. The method according to claim 1, wherein the at least one clay particulate component is present in an amount of not more than 15 wt.-% of the overall composition.

5. The method according to claim 1, wherein the at least one phyllosilicate and/or the overall composition has an oil absorption of more than about 90 g/100 g.

6. The method according to claim 1, wherein the at least one clay particulate component has a particle size of at least 600 µm and less than 5 mm.

7. The method according to claim 1, wherein the at least one clay particulate component is also a water absorbing component.

8. The method according to claim 1, wherein the at least one clay particulate component has an aspect ratio between 1 and 2.

9. The method according to claim 1, wherein the at least one clay particulate component has a substantially spherical shape.

10. The method according to claim 1, wherein the absorbent composition has a particle size D90 of not more than 300 µm.

11. The method according to claim 1, wherein the at least one phyllosilicate comprises at least 75 wt.~% of the overall composition.

12. The method according to claim 1, wherein the at least one phyllosilicate and/or the composition itself has a specific surface area of at least 100 $m^2/g$.

13. The method according to claim 1, wherein the at least one phyllosilicate and/or the overall composition has a water absorption of at least 35%.

14. The method according to claim 1, wherein the at least one phyllosilicate and/or the overall composition has an oil absorption of at least 25%.

15. The method according to claim 1, wherein the at least one phyllosilicate and/or the overall composition has a dynamic water adsorption of at least 8%.

16. The method according to claim 1, wherein the at least one phyllosilicate and/or the overall composition has a total pore volume of at least 0.2 ml/g.

17. The method according to claim 1, wherein the at least one phyllosilicate and/or the overall composition has a cation exchange capacity (CEC) of at least 30 meq/100 g.

18. The method according to claim 1, wherein the at least one clay particulate component has a swellability of less than 10 ml/2 g.

19. The method according to claim 1, wherein the at least one clay particulate component has an attrition value of less than 5%.

20. The method according to claim 1, wherein the absorbent composition further comprises at least one component selected from the group of fragrances or perfumes, biocides, fungicides, herbicides, sanitizers or fillers.

21. The method according to claim 1, wherein the composition has a pH value, measured in a suspension of 10 parts by weight of the composition in 100 parts by weight water, of at least about 8.

22. The method according to claim 1 wherein the animal is a pig, cattle, sheep, horses, goats or poultry.

23. The method of claim 1, wherein the clay particulate component having a particle size of at least 250 µm is one or more phyllosilicates.

* * * * *